United States Patent
Bernhardt

(10) Patent No.: US 6,499,320 B1
(45) Date of Patent: Dec. 31, 2002

(54) GARMENT HAVING ANTIMICROBIAL PROPERTIES AND ITS ASSOCIATED METHOD OF MANUFACTURE

(76) Inventor: Frederick S. Bernhardt, 705 Linton Ave., Croydon, PA (US) 19021

( * ) Notice: Subject to any disclaimer, the term of this patent is extended or adjusted under 35 U.S.C. 154(b) by 0 days.

(21) Appl. No.: 09/824,943

(22) Filed: Apr. 3, 2001

(51) Int. Cl.[7] .................................................. A43B 17/00
(52) U.S. Cl. ........................... 66/178 R; 66/202; 2/239
(58) Field of Search .............................. 66/202, 178 R, 66/196; 2/239, 409, 240, 241, 242

(56) References Cited

U.S. PATENT DOCUMENTS

| | | |
|---|---|---|
| 3,464,847 A | 9/1969 | Megson |
| 3,950,822 A | 4/1976 | Bolli |
| 4,206,514 A * | 6/1980 | Yamauchi .................... 66/202 |
| 4,672,825 A * | 6/1987 | Yasukawa et al. ............ 66/202 |
| 5,053,021 A * | 10/1991 | Feibus ......................... 66/202 |
| 5,651,244 A | 7/1997 | Lucca ............................. 57/75 |
| 5,799,333 A * | 9/1998 | Mcgarry et al. .............. 66/202 |
| 5,965,223 A * | 10/1999 | Andrews et al. ............. 66/202 |
| 6,155,084 A * | 12/2000 | Andrews et al. ............. 66/202 |

* cited by examiner

Primary Examiner—Danny Worrell
(74) Attorney, Agent, or Firm—LaMorte & Associates

(57) ABSTRACT

A garment device and its associated method of manufacture are claimed. The garment produced has an internal surface and an external surface, wherein the internal surface contacts a portion of the user's skin. The garment is preferably fabricated from a knitted or woven material having at least one first yarn made from a conventional garment material and a second yarn that includes an active antimicrobial agent. The knit pattern is designed to cause the conventional garment material to be predominant on the exterior surface of the garment while the yarns containing the antimicrobial agent are predominant on the interior surface of the garment. The presence of the yarns with the active antimicrobial agent on the interior of the garment resists the microbial contamination of the interior of the garment. As a result, the length of time the garment can be worn without the adverse effects of contamination can be extended.

12 Claims, 5 Drawing Sheets

GARMENT HAVING ANTIMICROBIAL PROPERTIES AND ITS ASSOCIATED METHOD OF MANUFACTURE

BACKGROUND OF THE INVENTION

1. Field of the Invention

The present invention relates to garments and the materials for garments that embody antimicrobial properties. More particularly, the present invention relates to garments and materials for garments that contain a metal such as silver, wherein the metal is the antimicrobial agent.

2. Prior Art Statement

There are many garments that are worn on the body that harbor bacterial and other microbial contamination. Socks are an obvious example. When socks are worn on the feet, the socks absorb perspiration. Furthermore, the sock becomes contaminated with microbial agents from the foot and shoe. The moist warm material of the sock is ideal for the growth of the microbial agents. As such, the socks quickly become malodorous and require laundering.

Typically, people only change their garments once a day. As the day progresses, the degree of microbial contamination within the garments increases. In addition to odor, microbial contamination has other adverse effects. The presence of the contaminated garment against the skin sometimes effects the health of the skin. People with sensitive skin may develop rashes, blisters and/or microbial infections transferred from the garments.

Another example of where a garment becomes quickly contaminated is a liner for a prosthetic limb. Liners are often placed over the remaining portion of an amputated limb prior to the attachment of a prosthesis to that limb. As a prosthesis is placed over the liner, the liner becomes encased in a dark, warm confined area. The liner quickly becomes contaminated with microbial agents from the skin. The liner harbors the microbial agents until laundered. The presence of the microbial agents causes the liner to become malodorous and often causes irritation to the skin. This requires a person to remove the prosthetic limb and change the liner more often than is convenient.

In the prior art, there exist many different ways to manufacture garment material so that it resists microbial contamination. One of the most common techniques used is to treat the material with an antimicrobial agent. Such prior art techniques are exemplified by U.S. Pat. No. 3,464,847 to Megson, entitled, Treatment Of Fabrics With Anthrantic Acid And Silver Nitrate Solutions. A problem associated with treating material with antimicrobial chemicals is that the antimicrobial chemicals tend to wash out of the material over time as the material is repeatedly laundered. Furthermore, the chemicals themselves may cause irritation to sensitive skin.

Another prior art technique used to resist microbial contamination of material is to manufacture the material from inorganic materials that do not absorb moisture or harbor bacteria. Garments made from such specialty materials tend to be more expensive than garments made of conventional materials. Furthermore, garments made from such materials tend to be less comfortable than garments made from conventional materials. Furthermore, although there exist many synthetic materials that do not harbor moisture and microbial contamination, these materials typically do no have antimicrobial properties that actively combat contamination.

A need therefore exists for a garment material that is comfortable, inexpensive and actively fights microbial contamination. This need is met by the present invention as it is described and claimed below.

SUMMARY OF THE INVENTION

The present invention is a garment device and its associated method of manufacture. The garment produced has an internal surface and an external surface, wherein the internal surface contacts a portion of the user's skin. The garment is preferably fabricated from a knitted or woven material having at least one first yarn made from a conventional garment material and a second yarn that includes an active antimicrobial agent. The knit pattern is designed to cause the conventional garment material to be predominant on the exterior surface of the garment while the yarns containing the antimicrobial agent are predominant on the interior surface of the garment. The presence of the yarns with the active antimicrobial agent on the interior of the garment resists the microbial contamination of the interior of the garment. As a result, the length of time the garment can be worn without the adverse effects of contamination can be extended.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE INVENTION

Although the present invention system can be used in conjunction with any garment worn over the skin, the present invention system is especially suitable for use in the manufacture of socks, stockings and prosthetic limb liners. As a result, the two exemplary embodiments of the present invention system will show the present invention system configured as a sock and a prosthetic limb liner in order to set forth two of the best modes contemplated for the invention.

Figure 1:
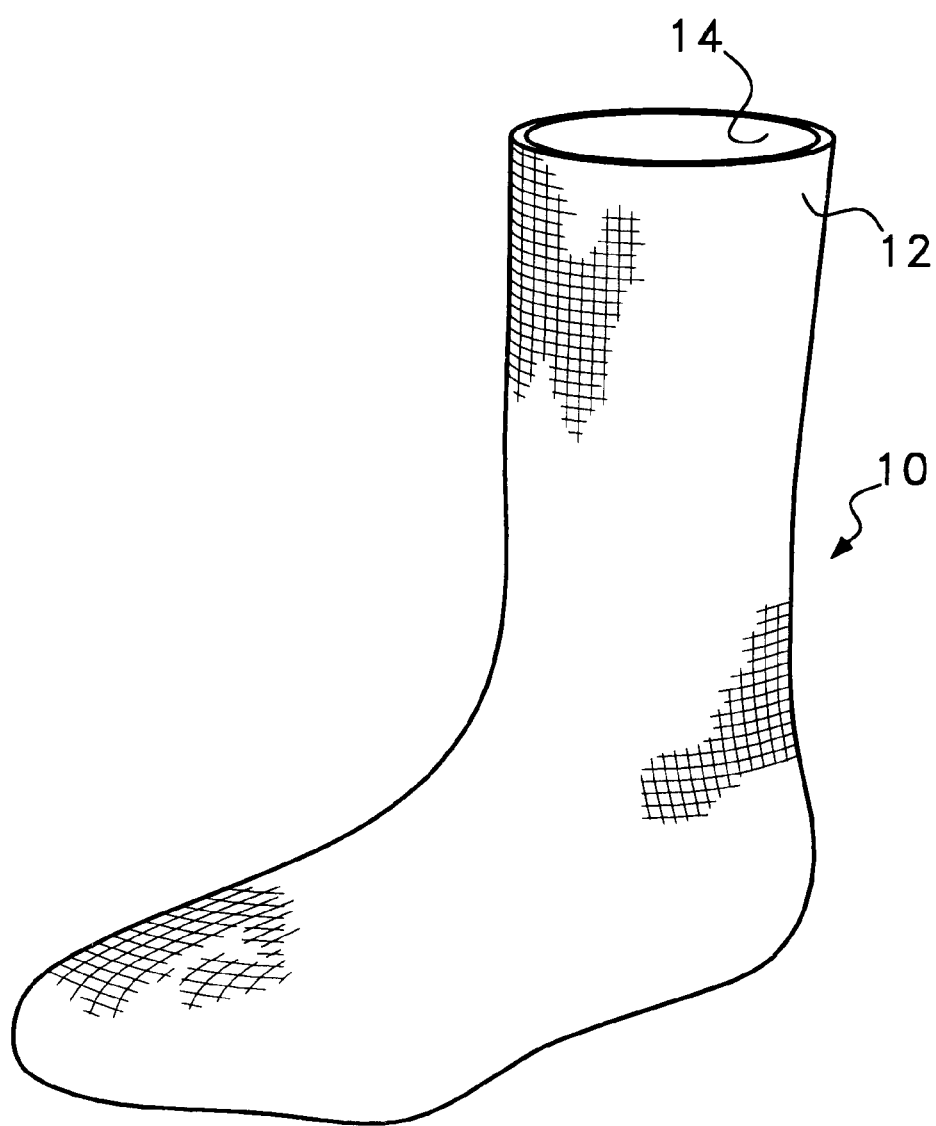
FIG. 1 is a perspective view of a sock made in accordance with the present invention.

Referring to FIG. 1, an exemplary embodiment of a sock 10 is shown in accordance with the present invention. The sock 10 is preferably of a knit manufacture and contains conventional sock yarn, such as cotton, silk, acrylic, wool, polyester or the like. The knit of the sock 10 also includes at least one antimicrobial yarn. The antimicrobial yarn that contains a nobel metal such as silver, copper or another metal that has antimicrobial properties. The production of knitting yarns that contain metal are disclosed in U.S. Pat. No. 5,651,244 to Lucca, entitled Ring Spinning Method And A Yarn Made Thereby; and U.S. Pat. No. 3,950,822 to Bolli, entitled Device For Manufacturing A Silver Used To Produce Jaspe Yarn, both of which are hereby incorporated into this disclosure by reference.

The sock 10 is preferably knitted in a manner so that the conventional sock yarns comprise the majority of the sock. Thus the sock can be manufactured at a low cost. However, the sock is knitted in a manner that also enables the antimicrobial yarn to be the predominant material that contacts the skin of the foot, even through the antimicrobial yarn is in a minority of the sock. As will later be described in more detail, the conventional sock yarns provide the majority of the structure of the sock. The antimicrobial yarn is configured in the knit pattern so that the antimicrobial yarn is predominant on the interior of the sock's structure. As a result, the exterior surface 12 of the sock 10 embodies conventional sock properties while the interior surface 14 of the sock embodies active antimicrobial properties.

The use of an antimicrobial yarn in a knit pattern is preferred because of the lower cost, lower degree of labor and overall quality of the material produced. However, other methods to create a sock with an antimicrobial agent on its interior exist. In alternate embodiments, it will be understood that a conventional sock can have its interior coated with an antimicrobial agent by either spraying or dipping the interior of the sock. Such alternate methods of production can be used in practicing the present invention.

Figure 2:
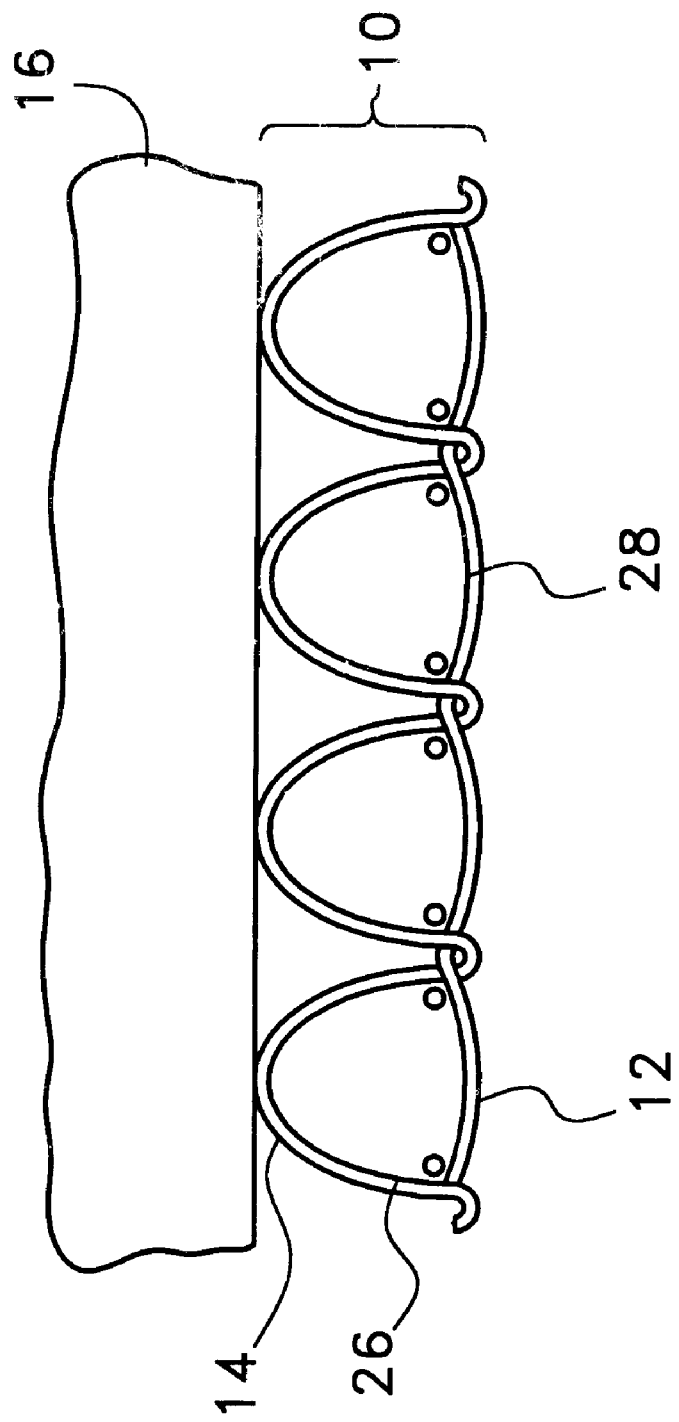
FIG. 2 is a cross-sectional view of an exemplary knit pattern used in creating the sock shown in FIG. 1.

Referring to FIG. 2, it will be understood that the knit material of the sock 10 contacts and cushions the skin 16 on the foot. The knit pattern of the sock 10 is created so that a large area of knitted loops 26 are created on the interior surface 14 of the sock 10. The loops 26 in the knit pattern help to cushion the skin of the foot 12 and distribute forces across the skin. The individual loops 26 conform to the contours of the foot 12. As has been previously mentioned, the antimicrobial yarn is used to create the loops 26 in conjunction with conventional yarns on the interior surface 14 of the sock. The antimicrobial yarns contain an antimicrobial metal, such as silver. As such, an antimicrobial yarn is the predominant material on the interior surface 14 of the sock 10.

The sock 10 also contains cross patterns of yarn 28 that are the predominant yarns on the exterior surface 12 of the sock 10. It is the cross pattern of yarns 28 that are made of conventional materials such as cotton, silk acrylic, wool, or polyester. Conventional materials are therefore the predominant material on the exterior surface 12 of the sock 10.

The sock knit pattern shown in FIG. 2 is merely exemplary. There are many different knitting patterns that can be used to commercially manufacture a sock, prosthesis liner or similar item. Prosthetic socks are typically commercially manufactured on programmable flatbed knitting machines. Traditional socks are typically produced on circular knitting machines. When producing socks, such machines are typically programmed to produce a fabric of plain jersey stitches having wavy horizontal loops on the interior and vertical column loops on the exterior. Conventional sock fabric made in such a manner usually forms narrow columns of close parallel wales on the exterior of the sock. The interior of the sock typically consists of wavy crosswise rows of loops separated from each other by slight depressions. By selectively combining antimicrobial yarns and conventional yarns, existing knitting machines can produce traditional socks where the antimicrobial yarn is predominant on the loop structures on the interior of the sock and the traditional yarns are predominant on the exterior of the sock.

In addition to traditional knit socks, seamless socks can also be produced using both antimicrobial yarns and conventional sock yarns. The method of producing a seamless socks with different types of yarns is shown in U.S. Pat. No. 5,737,943 to Bernhardt, the inventor herein, entitled, Seamless Pedorthic Sock And Method Of Knitting Same. This patent is incorporated into this specification by reference. The method of producing a sock disclosed in U.S. Pat. No. 5,737,943 uses multiple yarns, wherein a selected yarn becomes predominant on the interior of the sock. The method of producing a sock disclosed in U.S. Pat. No. 5,737,943 can be adapted for use with the present invention by utilizing an antimicrobial yarn as the selected yarn for the interior of the sock.

Figure 3:
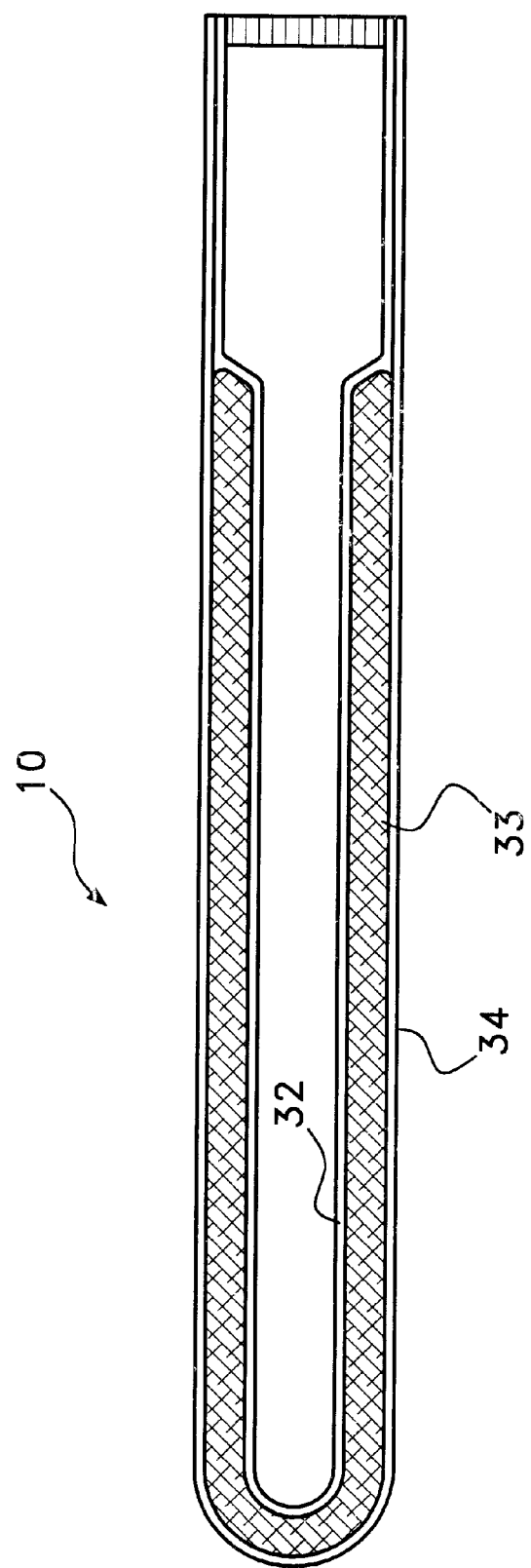
FIG. 3 is a perspective view of a prosthetic limb liner sock made in accordance with the present invention.

Referring to FIG. 3, an example of a prosthetic limb liner 30 is shown. The prosthetic limb liner 30 is used to illustrate that the present invention can be used for garments other than socks. The prosthetic limb liner 30 has a laminated structure, wherein an elastomeric material 33 is encased between an interior material surface 32 and an exterior material surface 34. The prosthetic limb liner 30 is pulled over the remaining portion of an amputated limb, prior to the attachment of a prosthetic limb. The interior material surface 32 contacts the skin of the person using the liner 30. The exterior material surface 34 contacts the prosthetic limb. The elastomeric material 33 conforms to any gaps that might exist between the amputated limb and the prosthetic limb.

In utilizing the teachings of the present invention, the interior material surface 32 can be at least partially manufactured from an antimicrobial yarn. In producing the interior material surface 32, the antimicrobial yarn can be knitted to be predominant on the surface that touches the skin, or can be uniformly knitted into the interior material surface 32. In either event, the interior material surface 32 will actively combat microbial contamination against the skin when the limb liner 30 is worn. Accordingly, the limb liner will actively combat microbial contamination. As such, the limb liner 30 can be worn for longer periods of time without the adverse effects caused by the build up of microbial contamination.

Figure 4:
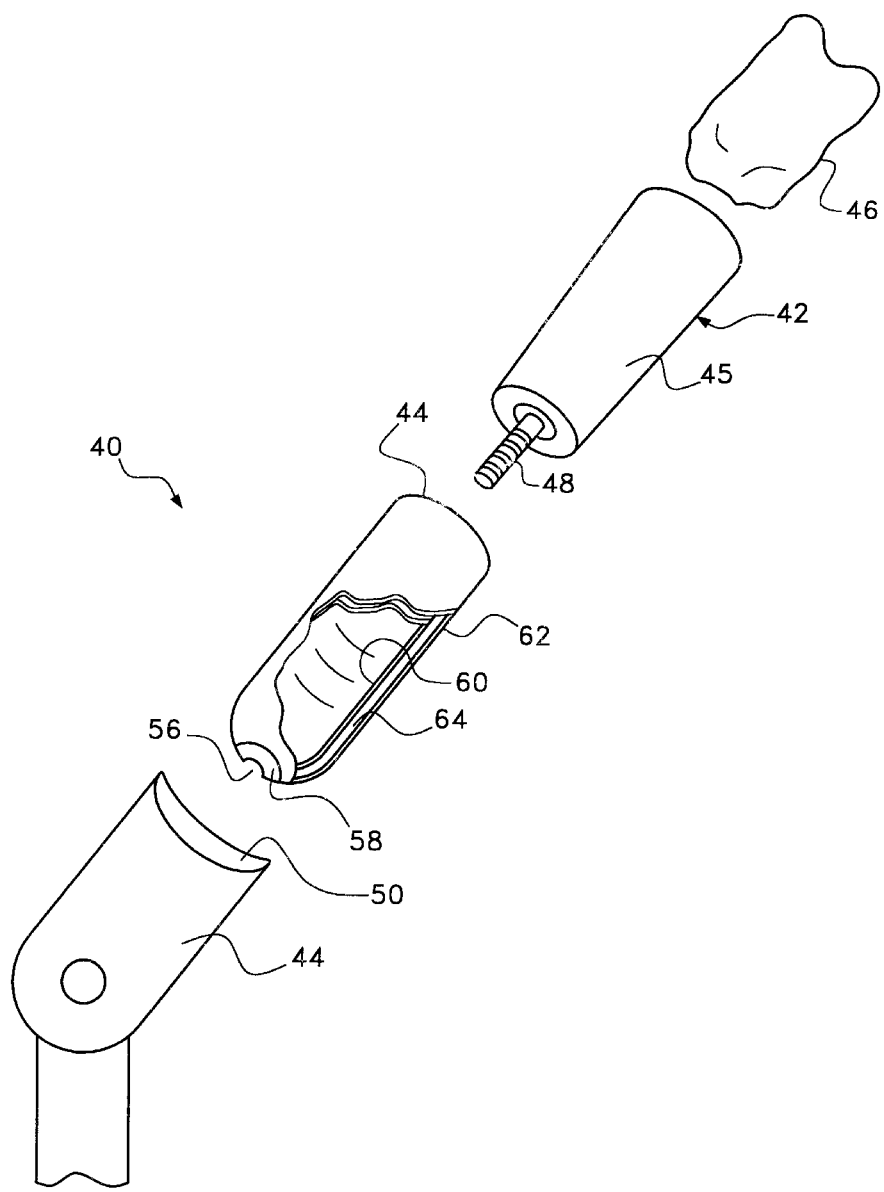
FIG. 4 is a perspective view of a prosthetic limb liner sock shown as part of the assembly that joins a prosthetic limb to an amputee.

Referring to FIG. 4, an exemplary embodiment of the present invention device 40 is shown in conjunction with a traditional limb liner 42 and a segment of a limb prosthesis 44. The limb liner 42 has an elastomeric body 45 that can be pulled over the limb stump 46 of an amputee. Once in place over the limb stump 46, the elastomeric body 45 of the limb liner 42 conforms to the configuration of the limb stump 46. A metal locking pin 48 extends forwardly from the apex of the limb liner 42. It is the metal locking pin 48 that is physically engaged by the limb prosthesis 44.

The limb prosthesis 44 contains a socket 40 that is shaped to mate with the limb liner 42 when the limb liner 42 is present over the limb stump 46.

The present invention liner sock 40 is a generally tubular structure having a first end 52 and a second end 54. The first end 52 of the liner sock 40 defines a small aperture 56. The aperture 56 is reinforced by at least one reinforcement patch 58. The second end 54 of the liner sock 40 is fully open. The second end 54 of the liner sock 40 is sized to fit over the limb liner 42 so that the liner sock 40 can be pulled over the limb liner 42. The aperture 56 at the first end 52 of the liner sock 40 is sized to enable the locking pin 48 of the limb liner 42 to pass therethrough.

The illustrated liner sock 40 has a laminated construction. The inner most layer 60 of the liner sock 40 is fabric, wherein fabric refers to either woven or knitted yarns. The inner layer of fabric 60 extends from the first end 62 of the liner sock 40 to the second end 54 of the liner sock 40. The inner layer of fabric 60 either contains silver yarn or is coated in silver or another antimicrobial agent. The outer most layer 62 of the liner sock 40 is also fabric. The outer most layer of fabric 62 also extends the full length of the liner sock 40 from the first end 52 of the liner sock 40 to the second end 54 of the liner sock 40. The outer most layer of fabric 62 also contains some silver yarns or is coated in silver. The inner layer of fabric 60 and the outer layer of fabric 62 are coupled together at the second end 54 of the liner sock 40 with a joining stitch, adhesive or some other coupling means.

An elastomeric material 64 is interposed between the inner layer of fabric 60 and the outer layer of fabric 62. The elastomeric material 64 is bonded to both the outer layer of fabric 62 and the inner layer of fabric 60. The elastomeric material 64 spreads when it is compressed. As a result, when the liner sock 40 is compressed between the limb liner 42 and the limb prosthesis 44, the elastomeric material 64 inside the liner sock 40 spreads from points of high compression into points of low compression. The result is a much more even pressure across the entire limb liner/limb prosthesis interface. Additionally, the elastomeric material 64 spreads to fill any voids at the limb liner/limb prosthesis interface. Accordingly, the elastomeric material 64 in the liner sock 40 compensates for any irregularities that exist between the limb liner 42 and the limb prosthesis 44. The limb prosthesis therefore fits better and can be worn in a more conformable manner despite any physiological changes that may occur in the limb stump over time. Microbial contamination at the various interface layers is suppressed by the material of the inner layer and outer layer of the liner sock 40.

The embodiment of FIG. 4, showed a liner sock made in accordance with the present invention. The liner sock is worn between a limb liner and the socket of a prosthesis. The principals of the present invention, however, can also be applied to the limb liner itself.

Figure 5:
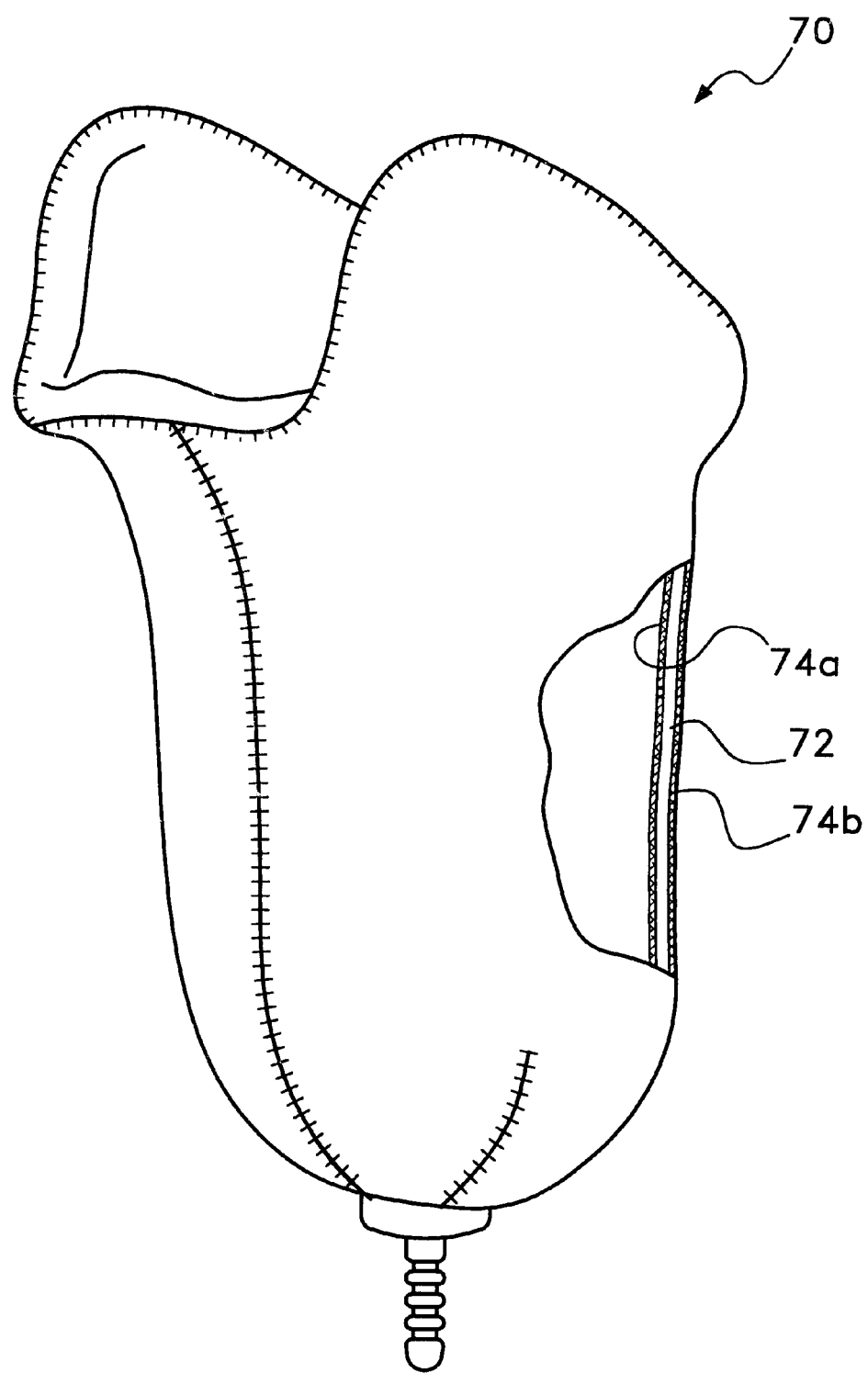
FIG. 5 is a perspective view of a prosthetic limb liner in accordance with the present invention.

Referring now to FIG. 5, a limb liner 70 is shown. The limb liner is fabricated from a synthetic elastomeric material 72 that is shaped to match the contours of the amputated stump. The elastomeric material 72 is lined on the interior and exterior with a knitted or woven material 74a, 74b. The knitted or woven material is tailored to match the contours of the core material 72 and may be adhesively bonded to the elastomeric material 72.

The interior and exterior fabric 74b contains yarns of silver, or are lined with silver. As such, the exterior fabric 74b embodies antimicrobial properties. The presence of silver at this interface prevents the build up of bacteria that can limit the amount of time the limb liner can be comfortably worn.

From the embodiments of the present invention illustrated, it will be understood that present invention can involve any garment that contacts the skin or the socket of a prosthetic limb. It will be understood that the embodiments of the present invention described and illustrated herein are merely exemplary and a person skilled in the art can make many variations to the embodiment shown without departing from the scope of the present invention. For example, although a knit pattern was illustrated, the present invention can be practiced with woven patterns as well. It should also be understood that the various elements from the different embodiments shown can be mixed together to create alternate embodiments that are not specifically described. All such variations, modifications and alternate embodiments are intended to be included within the scope of the present invention as defined by the appended claims.

What is claimed is:

1. A limb liner sock for use under a prosthetic limb, said limb liner sock comprising:

an interior layer of material, having an internally exposed surface, wherein said interior layer of material is knit from a first set of yarns and at least one yarn in said first set of yarns is an antimicrobial yarn that is coated with silver;

an exterior layer of material, having an externally exposed surface, wherein said exterior layer of material is knit from a second set of yarns;

elastomeric material disposed between at least one section of said interior layer of material and said exterior layer of material.

2. The liner sock according to claim 1, wherein said interior layer of material is knit in a predetermined pattern that make said antimicrobial yarn a predominant yarn on said internally exposed surface of said interior layer of material.

3. The liner sock according to claim 1, wherein said second set of yarns contains at least one silver coated yarn.

4. The liner sock according to claim 1, wherein said elastomeric material is bonded to said interior layer of material and said exterior layer of material in said at least one section.

5. The liner sock according to claim 1, wherein said liner contains a first section and a second section, and wherein elastomeric material is disposed between said interior layer of material and said exterior layer of material in said second section.

6. The liner sock according to claim 5, wherein said interior layer of material is joined directly to said exterior layer of material in said first section of said liner sock.

7. The liner sock according to claim 1, wherein said liner is tubular in shape, having an open end and a closed bottom end.

8. The liner sock according to claim 7, wherein an aperture is disposed in said closed bottom end of said liner sock, wherein said aperture extends through said inner layer of material, said outer layer of material and said elastomeric material disposed therebetween.

9. A limb liner to be worn on an amputated limb stump to enable a prosthetic limb to be worn on the limb stump, said limb liner comprising:

an elastomeric structure formed to match and receive the limb stump, said elastomeric structure having an interior surface that receives the limb stump and an exterior surface;

an interior layer of material bonded to said interior surface of said elastomeric structure, wherein said interior layer of material contains silver; and an exterior layer of material bonded to said exterior surface of said elastomeric structure.

10. The liner according to claim 9, wherein said exterior layer of material contains silver.

11. The liner according to claim 9, wherein said interior layer of material is knit from a set of yarns that contain at least one silver coated yarn.

12. The liner according to claim 11, wherein said interior layer of material is knit in a predetermined pattern that make said antimicrobial yarn a predominant yarn on said internally exposed surface of said interior layer of material.

\* \* \* \* \*